(12) United States Patent
Behzadi et al.

(10) Patent No.: US 7,969,161 B2
(45) Date of Patent: Jun. 28, 2011

(54) OPTIMAL DRIVE FREQUENCY SELECTION IN ELECTRICAL TOMOGRAPHY

(75) Inventors: Yashar Behzadi, San Francisco, CA (US); Kenneth C. Crandall, Sunnyvale, CA (US)

(73) Assignee: Proteus Bomedical, Inc., Redwood City, CA (US)

( * ) Notice: Subject to any disclaimer, the term of this patent is extended or adjusted under 35 U.S.C. 154(b) by 0 days.

(21) Appl. No.: 12/665,514

(22) PCT Filed: Dec. 1, 2009

(86) PCT No.: PCT/US2009/066251
§ 371 (c)(1),
(2), (4) Date: Dec. 18, 2009

(87) PCT Pub. No.: WO2010/065539
PCT Pub. Date: Jun. 10, 2010

(65) Prior Publication Data
US 2011/0001488 A1    Jan. 6, 2011

Related U.S. Application Data

(60) Provisional application No. 61/119,345, filed on Dec. 2, 2008.

(51) Int. Cl.
*G01R 29/26* (2006.01)
*A61B 5/05* (2006.01)
(52) U.S. Cl. ........................ 324/613; 600/547
(58) Field of Classification Search .................. 324/613, 324/614; 600/547
See application file for complete search history.

(56) References Cited

U.S. PATENT DOCUMENTS

| | | | |
|---|---|---|---|
| 4,182,315 A | 1/1980 | Vas et al. |
| 5,243,976 A | 9/1993 | Ferek-Petric et al. |
| 5,544,656 A | 8/1996 | Pitsillides et al. |
| 5,628,777 A | 5/1997 | Moberg et al. |
| 5,662,108 A | 9/1997 | Budd et al. |

(Continued)

FOREIGN PATENT DOCUMENTS
EP    1321097    6/2003
(Continued)

OTHER PUBLICATIONS

"Implant" Merriam Webster Online Dictionary (2009) Merriam-Webster Online. <http://www.merriam-webster.com/dictionary/implant>.

(Continued)

*Primary Examiner* — Timothy J Dole
(74) *Attorney, Agent, or Firm* — Bret E. Field; Bozicevic Field & Francis LLP

(57) ABSTRACT

Electrical tomography drive frequency selection systems and methods are disclosed. One aspect of the present invention pertains to a system for optimally selecting a drive frequency of an electrical tomography which comprises a sensor electrode stably associated with a tissue site within an internal organ of a subject for generating an induced signal based on a noise signal over a range of frequency bands, wherein an electrical field for the electrical tomography is turned off. In addition, the system comprises a noise processing module for isolating the induced signal for each frequency band over the range of frequency bands. Furthermore, the system comprises a frequency select module for selecting a drive frequency of the electrical field for the electrical tomography by comparing the induced signal for each frequency band over the range of frequency bands.

29 Claims, 7 Drawing Sheets

U.S. PATENT DOCUMENTS

| | | | |
|---|---|---|---|
| 5,852,784 A * | 12/1998 | Ito et al. .................... 455/552.1 |
| 5,861,008 A * | 1/1999 | Obel et al. ...................... 607/11 |
| 5,983,126 A | 11/1999 | Wittkampf |
| 5,991,661 A | 11/1999 | Park et al. |
| 6,002,963 A | 12/1999 | Mouchawar et al. |
| 6,009,349 A | 12/1999 | Mouchawar et al. |
| 6,026,325 A | 2/2000 | Weinberg et al. |
| 6,044,299 A | 3/2000 | Nilsson |
| 6,259,937 B1 | 7/2001 | Schulman et al. |
| 6,263,248 B1 | 7/2001 | Farley et al. |
| 6,295,324 B1 * | 9/2001 | Whikehart .................... 375/308 |
| 6,295,464 B1 | 9/2001 | Metaxas |
| 6,298,257 B1 | 10/2001 | Hall et al. |
| 6,346,124 B1 | 2/2002 | Geiser et al. |
| 6,473,638 B2 | 10/2002 | Ferek-Petric |
| 6,477,406 B1 | 11/2002 | Turcott |
| 6,493,575 B1 | 12/2002 | Kesten et al. |
| 6,625,493 B2 | 9/2003 | Kroll et al. |
| 6,731,970 B2 | 5/2004 | Schlossbauer et al. |
| 6,795,732 B2 | 9/2004 | Stadler et al. |
| 6,889,084 B2 | 5/2005 | Thompson et al. |
| 6,892,092 B2 * | 5/2005 | Palreddy et al. .............. 600/509 |
| 6,950,689 B1 | 9/2005 | Willis et al. |
| 7,127,289 B2 | 10/2006 | Yu et al. |
| 7,130,681 B2 | 10/2006 | Gebhardt et al. |
| 7,148,701 B2 * | 12/2006 | Park et al. .................... 600/547 |
| 7,263,398 B2 | 8/2007 | Carr |
| 7,269,460 B2 | 9/2007 | Chinchoy |
| 7,711,418 B2 * | 5/2010 | Garber et al. ................. 600/547 |
| 2003/0065365 A1 | 4/2003 | Zhu et al. |
| 2003/0100925 A1 | 5/2003 | Pape et al. |
| 2004/0077952 A1 | 4/2004 | Rafter et al. |
| 2004/0172078 A1 | 9/2004 | Chinchoy |
| 2004/0193021 A1 | 9/2004 | Zdeblick et al. |
| 2004/0243192 A1 | 12/2004 | Hepp et al. |
| 2005/0038481 A1 | 2/2005 | Chinchoy et al. |
| 2005/0043895 A1 | 2/2005 | Schechter |
| 2005/0059901 A1 | 3/2005 | Garber et al. |
| 2005/0215914 A1 | 9/2005 | Bornzin et al. |
| 2006/0004301 A1 | 1/2006 | Kasevich et al. |
| 2006/0058588 A1 | 3/2006 | Zdeblick |
| 2006/0116581 A1 | 6/2006 | Zdeblick et al. |
| 2006/0116599 A1 | 6/2006 | Davis |
| 2006/0235480 A1 | 10/2006 | Schecter |
| 2007/0010758 A1 | 1/2007 | Matthiessen et al. |
| 2007/0123944 A1 | 5/2007 | Zdeblick |
| 2007/0135721 A1 | 6/2007 | Zdeblick |
| 2007/0161894 A1 | 7/2007 | Zdeblick et al. |
| 2007/0167758 A1 | 7/2007 | Costello |
| 2008/0058656 A1 | 3/2008 | Costello et al. |
| 2008/0183072 A1 | 7/2008 | Robertson et al. |
| 2008/0208068 A1 | 8/2008 | Robertson et al. |
| 2008/0224688 A1 * | 9/2008 | Rubinsky et al. .......... 324/76.77 |
| 2008/0252304 A1 | 10/2008 | Woo et al. |
| 2008/0294218 A1 | 11/2008 | Savage et al. |
| 2009/0036769 A1 | 2/2009 | Zdeblick |
| 2009/0148385 A1 | 6/2009 | Willard et al. |

FOREIGN PATENT DOCUMENTS

| | | |
|---|---|---|
| EP | 1503823 | 5/2006 |
| WO | 03/097160 | 11/2003 |
| WO | 2006029090 | 3/2006 |
| WO | 2006042039 | 4/2006 |
| WO | 2006/069322 | 6/2006 |
| WO | 2006/104869 | 10/2006 |
| WO | 2006/105394 | 10/2006 |
| WO | 2006/113659 | 10/2006 |
| WO | 2006105474 | 10/2006 |
| WO | 2007/075974 | 7/2007 |

OTHER PUBLICATIONS

Iskander et al., "Electromagnetic Techniques for Medical Diagnosis: A Review" Prceedings of the IEEE, Vo. 68, No. 1 (1980) 126-133.

Lee et al., "A Microprocessor-Based Noninvasive Arterial Pulse Wave Analyzer" IEEE Transactions on Biomedical Engineering (1985) 32(6): 451-455.

U.S. Appl. No. 12/522,537, filed Jul. 8, 2009; Arne et al., "Continous Field Tomography Stystems and Methods of Using the Same".

Sermesant et al., "An electromechanical model of the heart for image analysis and simulation" ISEE Transactions on Medical Imaging (2006) 25:612-625.

Sermesant et al., "Stimulation of cardiac pathologies using an electromechanical biventricular model and XMR interventional imaging" Medical Image Analysis (2005) 9:467-480.

Usyk et al., "Electromechanical Model of Cardiac Resynchronization in the Dilated Failing Heart with Left Bundle Branch Block" J. Electrocardiology (suppp 2003) 36: 57-61.

* cited by examiner

OPTIMAL DRIVE FREQUENCY SELECTION
IN ELECTRICAL TOMOGRAPHY

RELATED APPLICATION AND CROSS REFERENCE

This application claims the benefit of U.S. Provisional Application Ser. No. 61/119,345 filed on Dec. 2, 2008, the entire disclosure of which is incorporated herein by reference.

FIELD OF THE INVENTION

Aspects of the present invention relate to the field of electronics. More particularly, aspects of the present invention relate to methods and systems of electrical tomography.

INTRODUCTION

Electrical tomography generally refers to imaging by sections or sectioning using an electrical field. In an electrical tomography system, an electrical field generator may generate the electrical field which is applied to a subject, e.g., a patient. In an electrical tomography (ET) system, a sensor electrode may be associated with a tissue site, e.g., an electrical lead having the sensor electrode physically associated with an organ. The sensor electrode then generates an induced signal in response to the electrical field applied to it. The induced signal, which corresponds to displacement of the sensor electrode or the tissue site, is forwarded to a signal processing module which processes the induced signal for various applications. By processing the induced signal, the displacement, velocity, and/or other data associated with the sensor electrode or the movement of the tissue site may be obtained.

In the ET system, the electrical field may be generated by at least one pair of drive electrodes which applies a continuous signal of a drive frequency. The drive frequency is currently selected arbitrarily. Thus, the presence of noise or interferences in the bandwidth of the drive frequency may affect the accuracy of the induced signal generated by the sensor electrode. Accordingly, the inherent noise or background signal may degrade the signal to noise ratio (SNR) and/or reduce the accuracy of the data derived from or otherwise associated with the induced signal.

SUMMARY

The present invention may address at least one of the foregoing issues with provision of systems and methods of optimal drive frequency selection in electrical tomography. By using the aspects of the present invention, the drive frequency of the signal used to generate the electrical field of the ET system can be optimally selected. Multiple techniques can be used to quantify in-band noise. An analog or digital spectrum analyzer can be used to measure the power within a particular frequency band over a wide range of frequencies. Additionally, the receiver or demodulator of the signal processing module of the ET system can be used to select the drive frequency. This can be achieved by sweeping the carrier frequency of the demodulator over a wide range of frequency bands. The demodulated signal amplitude and standard deviation obtained through the two techniques can be used to select the drive frequency with the least noise present.

BRIEF DESCRIPTION OF THE DRAWINGS

Example aspects are illustrated by way of example and not limitation in the figures of the accompanying drawings, in which like references indicate similar elements and in which.

Figure 1:
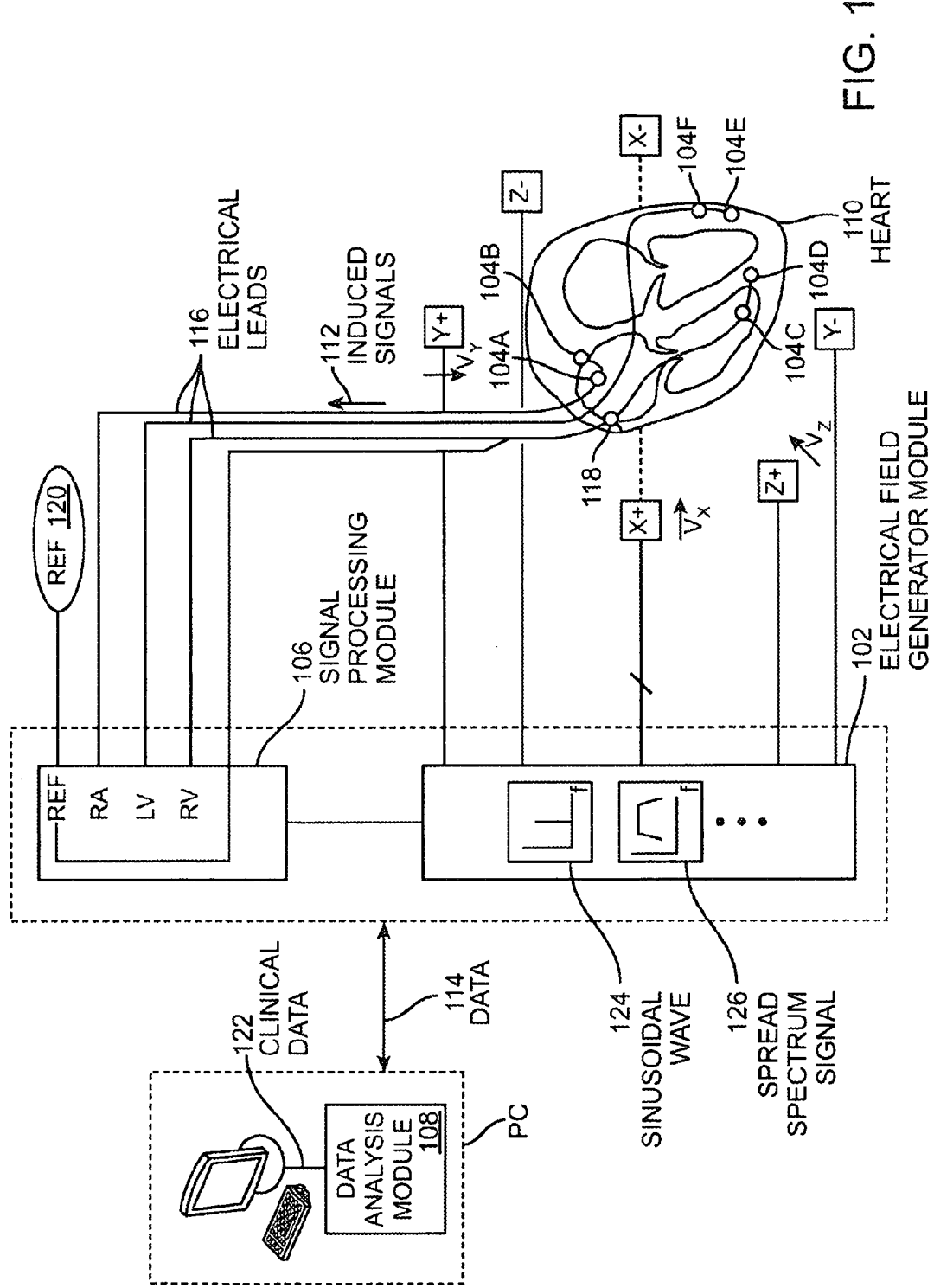
FIG. 1 illustrates an exemplary electrical tomography (ET) system, according to an aspect of the present invention.

Other features of the present aspects will be apparent from the accompanying drawings and from the detailed description that follows.

DETAILED DESCRIPTION

Reference will now be made in detail to the aspects of the invention, examples of which are illustrated in the accompanying drawings. While the invention will be described in conjunction with the aspects, it will be understood that they are not intended to limit the invention to these aspects. On the contrary, the disclosure is intended to cover alternatives, modifications and equivalents, which may be included within the spirit and scope of the invention. Furthermore, in the detailed description, numerous specific details are set forth in order to provide a thorough understanding of the present disclosure. However, it will be obvious to one of ordinary skill in the art that the present disclosure may be practiced without these specific details. In other instances, well known methods, procedures, components, and circuits have not been described in detail as not to unnecessarily obscure aspects of the present invention.

In continuous field tomography, a continuous field sensing element, e.g., a sensor electrode, probe, etc., is stably associated with a tissue location, and a change in the continuous field sensed by the sensing element is employed for evaluation purposes, e.g., identification and measurement of tissue movement. Various methods, devices, and/or systems associated with continuous field tomography, as well as data derived thereby, are described in PCT Patent Application Ser. No. PCT/US2005/036035 filed Oct. 6, 2005, also filed as U.S. patent application Ser. No. 11/664,340 filed Mar. 30, 2007, U.S. patent application Ser. No. 11/731,786 filed Mar. 30, 2007, and U.S. patent application Ser. No. 11/731,726 filed Mar. 30, 2007, each of the foregoing herein incorporated by reference in its entirety for all purposes.

Aspects of the present invention can derive data using several types of continuous fields. For example, an electrical tomography system may apply an electrical field of a sinusoidal wave. In general, the field magnitude can be expressed as:

$$F_0 = A \cdot \sin(2\pi \cdot f \cdot t + \phi)$$

where A is the field amplitude, f is the frequency at which the field oscillates, t is the time, and $\phi$ is the phase shift.

When a tissue region is subject to such a field, and when a sensing element, such as an electrode, resides in the same region, e.g., by being stably associated therewith, the field can induce a signal upon the sensing element. The induced signal may be of the form:

$$S = B \cdot \sin(2\pi \cdot f' \cdot t + \phi')$$

where B is the amplitude of the induced signal, f' is the induced signal's frequency, and $\phi'$ is the induced signal's phase shift. In one aspect, of interest is a transformation function "T", which can be determined from S and $F_o$ using the following relationship: $S = T(x,y,z,t)°F_o$. Thus, tissue location movement may be evaluated by detecting a transformation of the continuous field. Because B, f', and $\phi'$ may depend upon the sensing element's location or movement in the field, one can perform tomography based on one or more of these values.

For example, if a continuous electrical field driven by an alternating-current (AC) voltage is present in a tissue region, an induced voltage may be detected on a sensor electrode therein. The frequency of the induced voltage, f', is the same as the frequency of the electrical field. The amplitude of the induced signal, however, varies with the location of the sensor electrode. By detecting the induced voltage and by measuring the amplitude of the signal, the location as well as the velocity of the sensor electrode can be determined.

It is appreciated that other types of signal sources can be used to generate the continuous electrical field. For instance, a spread spectrum signal, e.g., Frequency-hopping spread spectrum (FHSS), direct-sequence spread spectrum (DSSS), time-hopping spread spectrum (THSS), chirp spread spectrum (CSS), and combinations of these techniques, may be used in place of the sinusoidal wave.

FIG. 1 illustrates an exemplary ET system, according to an aspect of the present invention. In FIG. 1, the electrical tomography system comprises an electrical field generator module 102, one or more sensor electrodes 104A-F, a signal processing module 106, and a data analysis module 108.

The electrical field generator module 102 generates one or more continuous electric fields and applies them to a subject, e.g., a patient, during an electrical tomography process. The sensor electrodes 104A-F are stably positioned on several tissue sites within an internal organ, e.g., in the right atrium (RA), left ventricle (LV), and/or right ventricle (RV) of a heart 110, of the subject. In one aspect, the continuous electric fields, e.g., $v_x$, $v_y$, $v_z$, etc., comprise three orthogonal electric fields along X-axis, Y-axis, and Z-axis. As each of the sensor electrodes 104A-F moves with the tissue movement, the peak-to-peak amplitude of the signal induced by each electric field may vary.

In FIG. 1, an AC voltage $v_x$ may be applied through a pair of drive electrodes, e.g., X+, X−, which may reside external or internal to the subject's body, in the x direction. Similarly, the ET system applies $v_y$ and $v_z$ in the direction through a pair of drive electrodes, e.g., Y+, Y−, and in the z direction through a pair of driving electrodes, e.g., Z+, Z−, respectively. Each of the $v_x$, $v_y$, and $v_z$ may operate at a different frequency. As a result, three induced signals 112, e.g., voltages, may present on each of the sensor electrodes 104A-F. Each induced signal also has a different frequency corresponding to the frequency of the electrical field or drive voltage, e.g., $v_x$, $v_y$, $v_z$, etc., in each direction. It is appreciated that the induced signals 112 by the sensor electrodes 104A-F may undergo change, e.g., may be amplitude-modulated, as the sensor electrodes 104A-F travel via the electric fields such as from the positive drive electrodes, e.g., X+, Y+, and Z+, to the negative drive electrodes, e.g., X−, Y−, and Z−. Therefore, by detecting the induced signals 112 using the signal processing module 106, the location of the sensor electrodes, e.g., 104A-F, can be determined in a three dimensional space.

In addition, the signal processing module 106 generates and forwards one or more data 114 associated with the sensor electrodes 104A-F based on induced signals 112 in response to the continuous electric fields. In one aspect, the data 114 may comprise displacement data of the electrodes 104A-F and/or their respective temporal data. As illustrated in FIG. 1, electrical leads 116 are used to forward signals from the electrodes 104A-F to the signal processing module 106. An electrode 118 may be used as a reference port, which may couple to an external voltage reference point 120, such as the ground. The data analysis module 108, which may be an application executable on a computer such as a PC, then generates clinical data 122 based on the data 114. In one aspect, the electrical field(s) may be based on a sinusoidal wave 124, a spread spectrum signal 126, or other types of signals.

It is appreciated that the system illustrated in FIG. 1 can be used to perform a similar operation on other physiologic systems such as the spinal column or internal organs, where the internal organ can be one of adrenals, appendix, bladder, brain, eyes, gall bladder, intestines, kidney, liver, lungs, esophagus, ovaries, pancreas, parathyroids, pituitary, prostate, spleen, stomach, testicles, thymus, thyroid, uterus, and veins. It is also appreciated that the electrical field generator module 102, the signal processing module 106, and the data analysis module 108 can be implemented in a single device or as individual devices.

It is also appreciated that the electrical fields applied to the subject may be in any number, e.g., one or more, and in any direction. It is further appreciated that the number of sensor electrodes and/or electrical leads used in the ET system may be varied.

Figure 2:
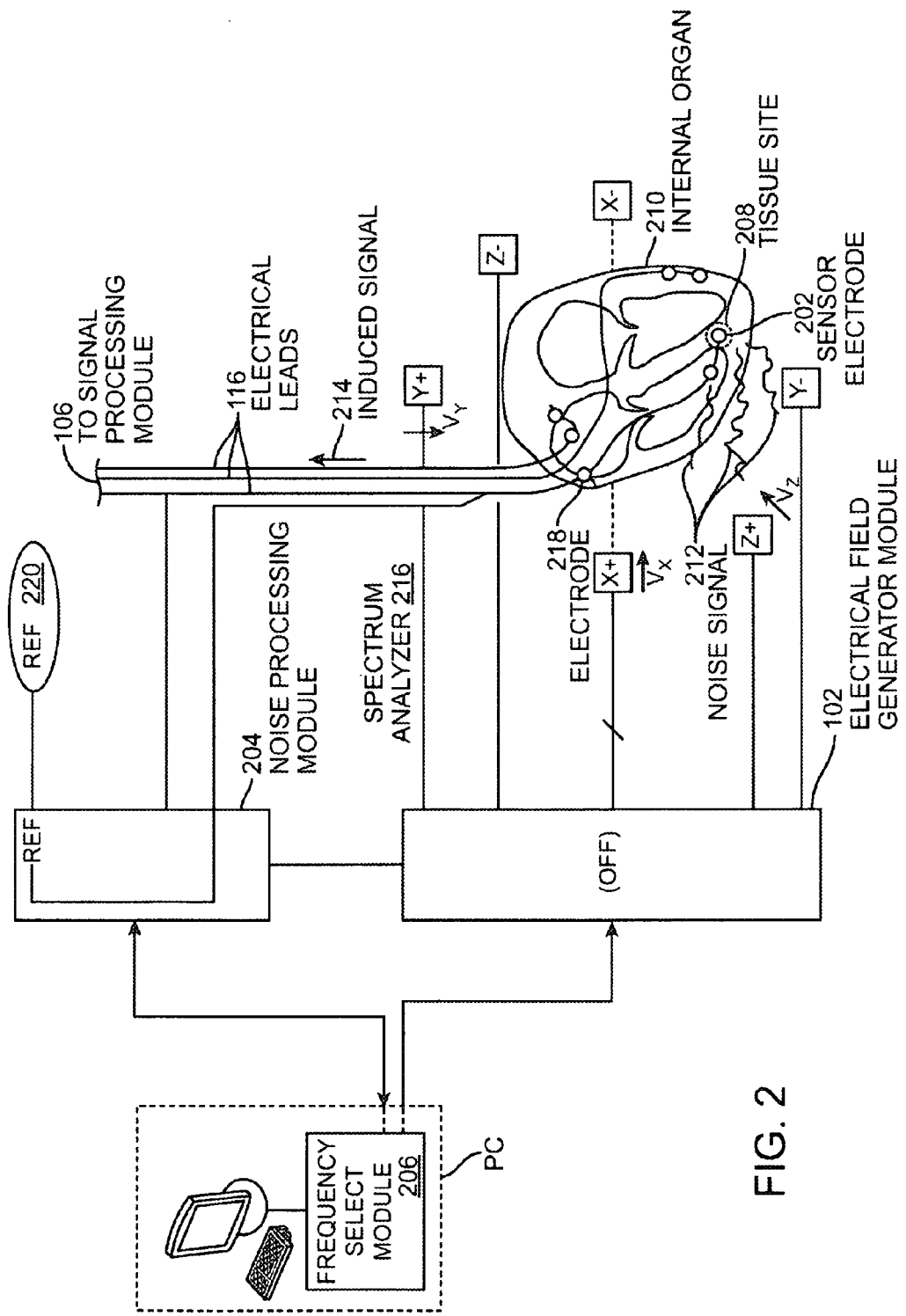
FIG. 2 illustrates an exemplary system for optimally selecting a drive frequency of the ET system of FIG. 1, according to an aspect of the present invention.

FIG. 2 illustrates an exemplary system for optimally selecting a drive frequency of the ET system of FIG. 1, according to an aspect of the present invention. The system for optimally selecting a drive frequency of the ET system comprises a sensor electrode 202, a noise processing module 204, and a frequency select module 206. In one aspect, the sensor electrode 202 is stably associated with a tissue site 208 of a living being, e.g., a person, a laboratory research animal, etc., for processing a noise signal 212, noises, interferences, etc., over a range of frequency bands, e.g., 50 KHz to 150 KHz. In various aspects, this operation may be performed to calibrate the ET system prior to turning on the electrical field for the ET and/or at predetermined points, e.g., time intervals to calibrate/re-calibrate after an initial calibration.

It is also appreciated that the noise signal 212 may be an unwanted sound or noise pollution. In electronics, noise can refer to the electronic signal corresponding to acoustic noise (in an audio system) or the electronic signal corresponding to the (visual) noise commonly seen as 'snow' on a degraded television or video image. In signal processing or computing it can be considered data without meaning; that is, data that is not being used to transmit a signal, but is simply produced as an unwanted by-product of other activities.

In one aspect, the noise processing module 204, e.g., receiver, is operable for separating or isolating an induced signal 214 for each frequency band over the range of frequency bands. The frequency select module 206, e.g., processor, is operable for selecting a drive frequency of the electrical field for the ET system of FIG. 1 by comparing the induced signal 214, e.g., its amplitude based on power, voltage, rms voltage, energy spectrum, over the range of frequency bands. It is appreciated that the frequency select module 206 can be implemented in software and/or hardware. It is also appreciated that the noise processing module 204 and/or the frequency select module 206 may reside in vivo or ex vivo. In FIG. 2, it is appreciated that the electrical field for each direction can be generated by its respective drive electrodes, e.g., X+, X−, Y+, Y−, Z+, Z−, etc. Once the drive frequency is determined, it may be used to generate the electrical field of the ET system applied to the subject, thus the sensor electrode 202 may perform an ET operation.

As illustrated in FIG. 2, the sensor electrode 202 is coupled to the noise processing module 204 via one or more electrical leads 116. In one aspect, the noise processing module 204 comprises a spectrum analyzer 216. It is appreciated that the spectrum analyzer 216 or spectral analyzer is a device used to examine an electrical, acoustic, or optical waveform and/or its power spectrum. The spectrum analyzer 216 may be an analog spectrum analyzer, which uses either a variable bandpass filter whose mid-frequency is automatically tuned, e.g., shifted, swept, etc., through the range of frequencies of which the spectrum is to be measured or a superheterodyne receiver where the local oscillator is swept through a range of frequencies, or a digital spectrum analyzer, which computes the Discrete Fourier Transform (DFT) or Fast Fourier Transform (FFT), a mathematical process that transforms a waveform into the components of its frequency spectrum. Since each of the electrical leads 116 may be exposed to the same noises or background signals, any one of the electrical leads 116 may be used to measure the noise level present in each frequency band.

In place of the commercial spectrum analyzer, a spectrum analysis device may be built as a part of the ET system. For instance, the device may be built which amplifies the induced signal 214, e.g., which is the noise signal 212 processed by the sensor electrode 202, and samples it with an analog to digital (A/D) converter at a regular interval to convert the signal into binary numbers. Those numbers are then accumulated in a memory and processed to obtain results of interest, e.g., frequency spectrum. Then, the stored samples are treated with fast Fourier transform to separate out frequency bands at the desired range. Then, the amount of energy or power in each band is sought for a relatively quiet, e.g., the quietest, drive frequency band.

Figure 6:
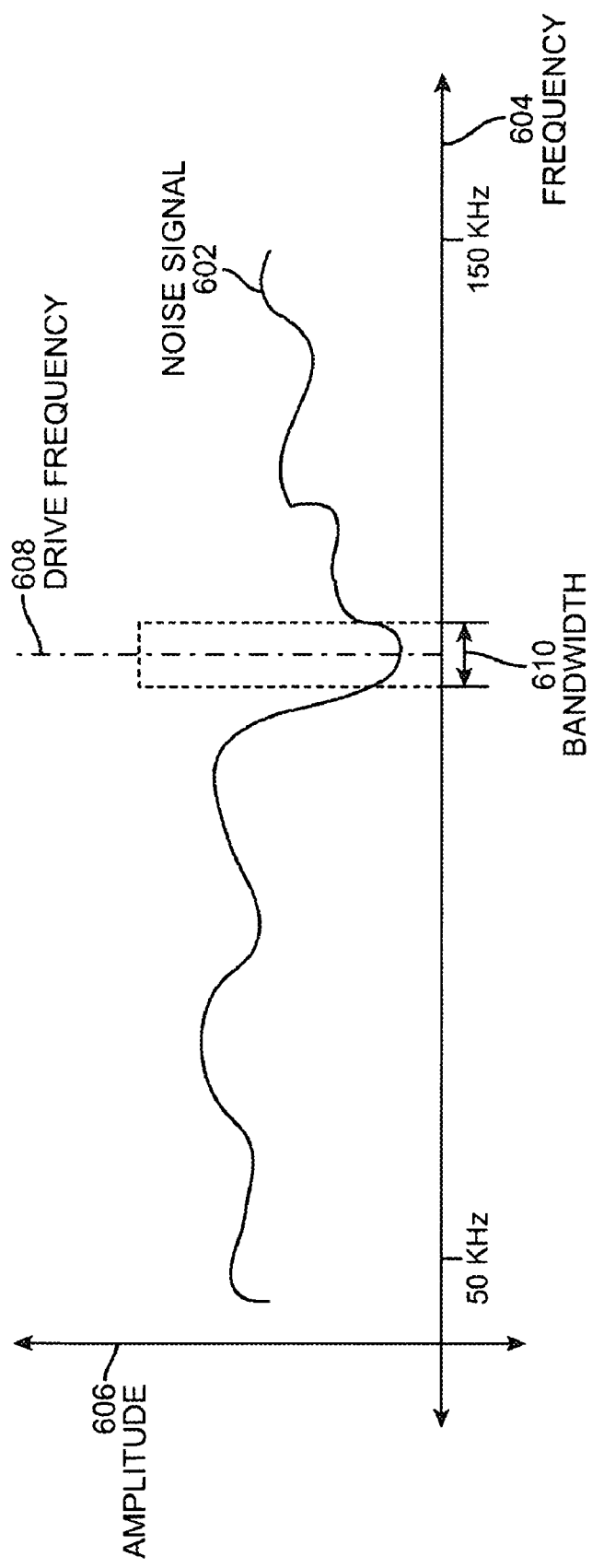
FIG. 6 illustrates an exemplary noise graph over a range of frequency bands, according to one aspect.

Based on the power spectrum of the induced signal 214, which is a signal induced due to the noise signal 212, a frequency band with a minimal instantaneous amplitude or standard deviation is selected as the drive frequency of the ET system among the frequency bands, as will be illustrated in detail in FIG. 6. With the selected drive frequency of a driving signal, e.g., a sinusoidal wave, a spread spectrum signal, etc., used to generate the electrical field of the ET system, the electrical field generator module 102 is ready to generate the electrical field with the drive frequency, which is less prone to noise in the neighborhood of target drive frequency. It is appreciated that an electrode 218 may be used as a reference port, which may couple to an external voltage reference point 220, such as the ground.

In an alternative aspect, a device for optimally selecting a drive frequency of an ET system comprises the noise processing module 204 for isolating the noise signal 212 for each frequency band over the range of frequency bands when the noise signal 212 is processed and forwarded by the sensor electrode 202 of the ET system stably associated with the tissue site 208 within the internal organ 210 of a subject as the induced signal 214. The device further comprises the frequency select module 206 for selecting a drive frequency of the electrical field for the ET by comparing the noise signal 212 for each frequency band over the range of frequency bands.

Figure 3:
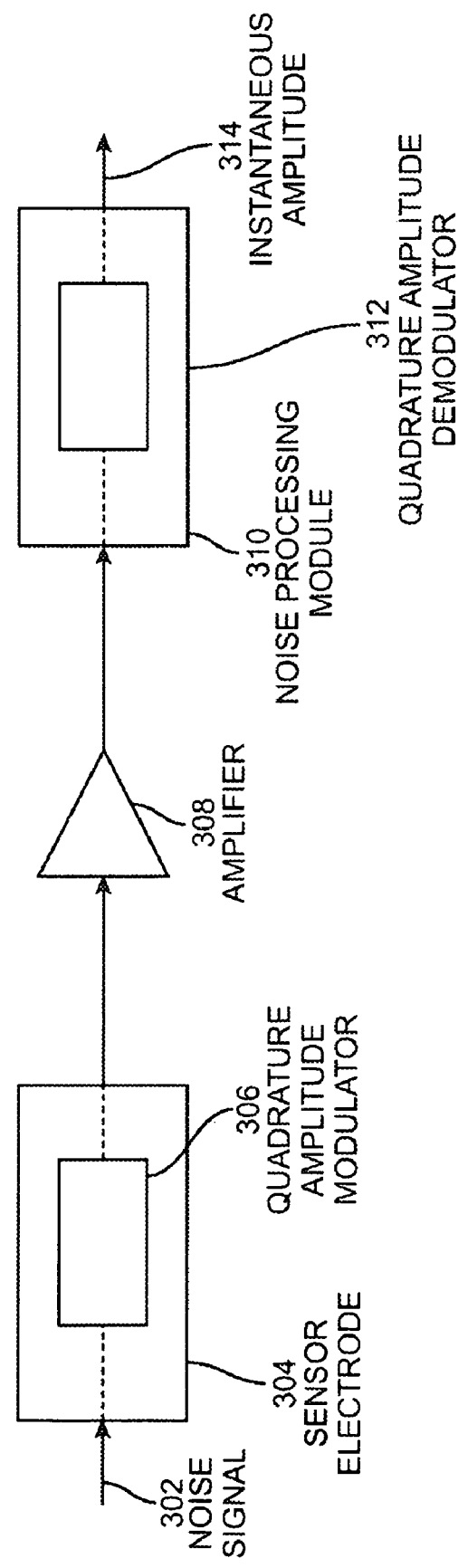
FIG. 3 illustrates an exemplary noise processing module for measuring the noise level detected by a sensor electrode of an ET system, according to an aspect of the present invention.

FIG. 3 illustrates an exemplary noise processing module for measuring the noise level detected by the sensor electrode 202 of the ET system of FIG. 2, according to an aspect of the present invention. It is appreciated that the noise processing module is an exemplary aspect of the noise processing module 204 of FIG. 2. As illustrated in FIG. 3, a sensor electrode 304 modulates a signal induced by a noise signal 302 and forwards the induced noise signal 302 to the noise processing module 310. In one aspect, a quadrature amplitude modulator 306 may be used to modulate the induced signal over the range of frequency bands. Quadrature amplitude modulation (QAM) is a modulation scheme which conveys data by changing (modulating) the amplitude of two carrier waves. These two waves, usually sinusoids, are out of phase with each other by 90° and are thus called quadrature carriers.

The QAM modulated induced signal, e.g., based on the noise signal 302, may be amplified via an amplifier 308 before it is processed by the noise processing module 310. The noise processing module 310 may comprise a quadrature amplitude demodulator 312. As will be illustrated in FIG. 4, the noise processing module 310 generates instantaneous amplitude 314 which corresponds to the noise signal 302 over the range of frequency bands. Thus, by comparing the instantaneous amplitude 314 or standard deviation based on one or more measurements, e.g., voltage, power, energy, etc., of each frequency band for the frequency range, the drive frequency of the ET system can be selected.

Figure 4:
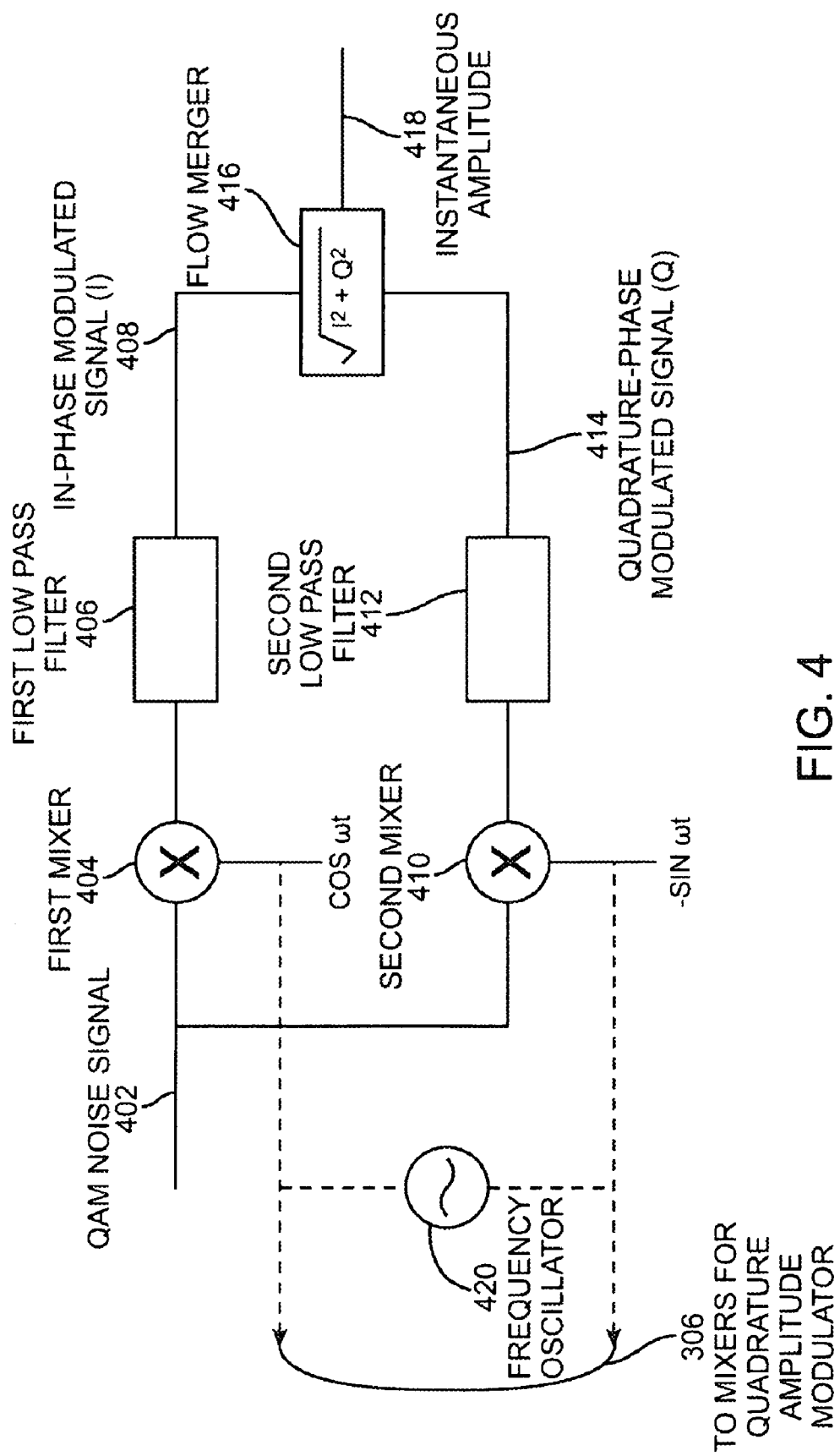
FIG. 4 illustrates a detailed block diagram of the noise processing module of FIG. 3, according to an aspect of the present invention.

FIG. 4 illustrates a detailed block diagram of the noise processing module of FIG. 3, according to an aspect of the present invention. The noise processing module comprises a first mixer 404 and a first low pass filter 406 coupled in series to demodulate an in-phase modulated signal (I) 408 and a second mixer 410 and a second low pass filter 412 to demodulate a quadrature-phase modulated signal (Q) 414.

As illustrated in FIG. 4, a quadrature amplitude modulated (QAM) noise signal 402 or a QAM induced signal is processed by the first mixer 404 and the second mixer 410. When the QAM noise signal 402, processed by the two mixers, passes through the first low pass filter 406 and the second low pass filter 408, the in-phase modulated signal (I) 408 and the quadrature-phase modulated signal (Q) 414 are generated. When the I 408 and Q 414 are processed by a flow merger 416, an instantaneous amplitude 418 may be obtained.

In one aspect, the noise processing module further comprises a frequency oscillator 420 coupled to the first mixer 404 and the second mixer 410 for sweeping across the range of the frequency bands. For example, the frequency oscillator 420 may be coupled to mixers of the quadrature amplitude modulator 306 of FIG. 3 and to the two mixers of the quadrature amplitude demodulator. Then, for a range of frequency bands, the frequency oscillator 420 may increase the carrier frequency of the mixers step by step to obtain instantaneous amplitudes which correspond to the different carrier frequencies. Accordingly, the drive frequency of the electrical field of the ET system may be obtained by selecting a frequency band with a minimal instantaneous amplitude among the frequency bands.

In one aspect, the standard deviation of the demodulated amplitude, e.g., the instantaneous amplitude 418, may be calculated for each of the frequencies stepped through using the frequency oscillator 420. It is appreciated that the standard deviation is the measure of noise or other interferences. Thus, by measuring the standard deviations of the combined power or voltage of the individual noises or interferences for all frequencies and selecting the frequency band with the lowest standard deviation, the most optimal drive frequency can be selected.

Figure 5:
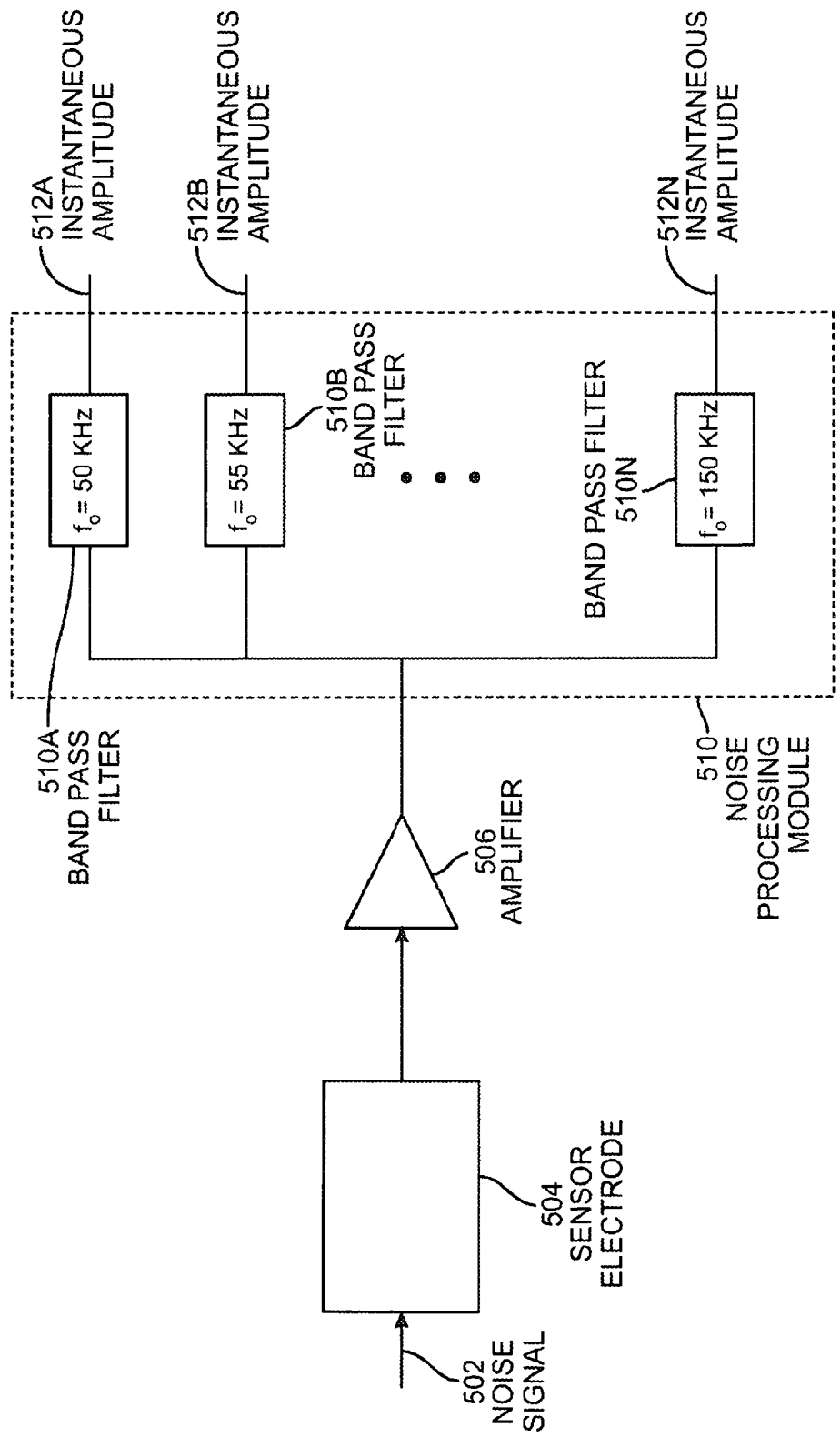
FIG. 5 illustrates an exemplary noise processing module for measuring the noise level detected by a sensor electrode of an ET system, according to an aspect of the present invention.

FIG. 5 illustrates an exemplary noise processing module 508 for measuring the noise level detected by the sensor electrode 202 of the ET system of FIG. 2, according to an aspect of the present invention. In FIG. 5, the noise processing module 508 comprises a plurality of band pass filters 510A-N with each band pass filter having a unique center frequency, e.g., 50 KHz, 55 KHz, 150 KHz, etc.

A noise signal 502 processed by a sensor electrode 504 is amplified before it is fed to the noise processing module 508. As the noise signal 502 is processed by the band pass filters 510A-N, instantaneous amplitudes 512A-N of the noise signal 502 over the range of frequency bands may be obtained. In one aspect, the drive frequency of the electrical field of the ET system is selected by selecting a frequency band with a minimal instantaneous amplitude among outputs of the band pass filters.

FIG. 6 illustrates an exemplary noise graph over a range of frequency bands, according to one aspect. In FIG. 6, a noise signal 602 is formed over a range of frequency 604. In one aspect, the range of frequency 604 is between 50 KHz and 150 KHz. As illustrated in FIG. 6, an amplitude 606 of the noise signal 602 may be different. In one aspect, the frequency select module 206 of FIG. 2 may select a drive frequency 608, where the drive frequency 608 has the lowest level of the noise signal 602. In one aspect, a bandwidth 610 of the drive frequency band comprises 100 KHz. Accordingly, by selecting the most optimal drive frequency band, signal to noise ratio (SNR) of the signal being processed by the ET system can be reached 20 dB or better.

Figure 7:
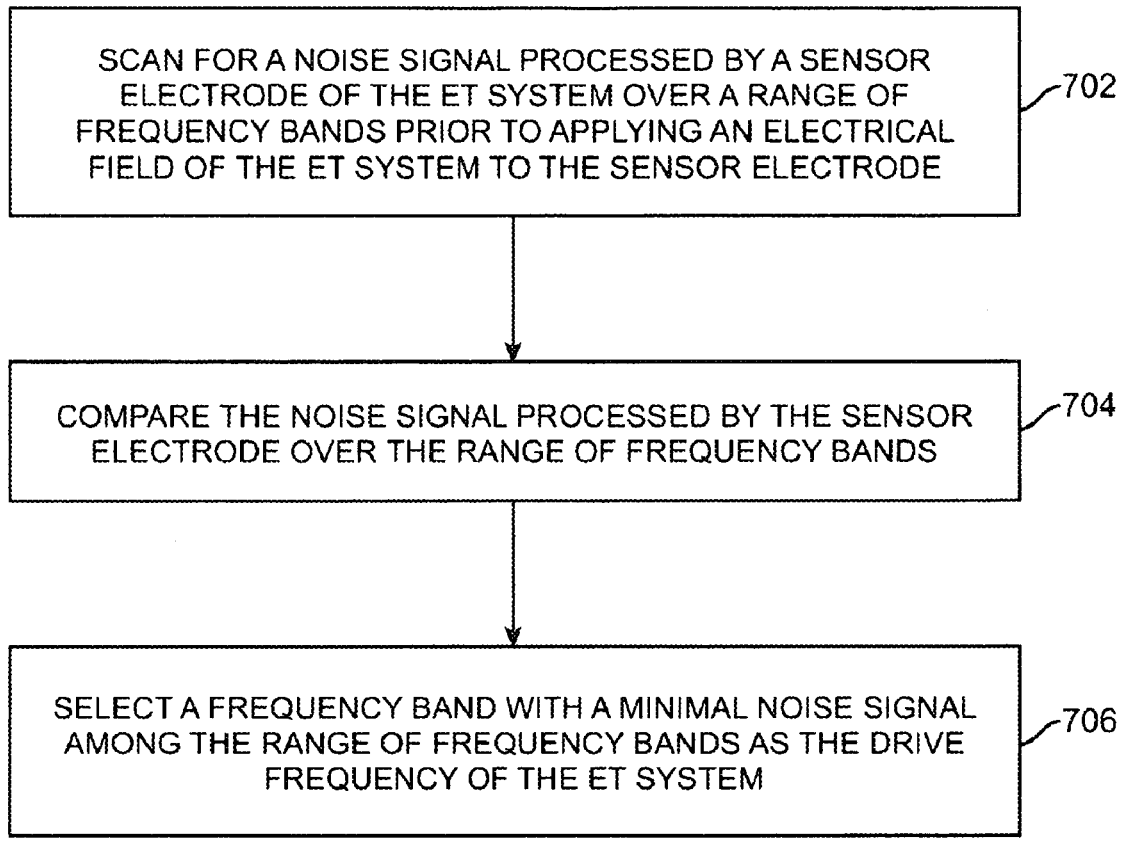
FIG. 7 is a process flow chart of an exemplary method for optimally selecting a drive frequency of an electrical tomography (ET) system, according to one aspect.

FIG. 7 is a process flow chart of an exemplary method for optimally selecting a drive frequency of an ET system, according to one aspect. In operation 702, a noise signal processed by a sensor electrode of the ET system is scanned over a range of frequency bands prior to applying an electrical field of the ET system to the sensor electrode. In operation 704, the noise signal processed by the sensor electrode over the range of frequency bands is compared. In operation 706, a frequency band with a minimal noise signal is selected among the range of frequency bands as the drive frequency of the ET system.

In one aspect, the noise signal is transmitted via an electrical lead. In addition, the scanning for the noise signal comprises performing a fast Fourier transform of the noise signal accessed at the electrical lead. Alternatively, the scanning for the noise signal comprises performing a discrete Fourier transform of the noise signal. In yet another aspect, the scanning for the noise levels comprises analyzing energy contents of the range of the frequency bands.

In one aspect, the range of the frequency bands is between 50 KHz and 150 KHz. In one aspect, a bandwidth of each frequency band comprises 100 Hz. In one aspect, selecting the drive frequency of the ET system is performed periodically, e.g., every 5 minutes, 10 minutes, etc. That is, if the current drive frequency happens to be one with a noise or background signal which generates a large voltage or power based on the periodic checking, then a neighboring frequency band with less noise is automatically selected as the drive frequency. In one aspect, the electrical field of the drive frequency is based on a sinusoidal wave, a spread spectrum signal, etc.

In various aspects, a device for optimally selecting a drive frequency of an electrical tomography system may comprise a sensor electrode and a frequency device.

The sensor electrode may process a noise signal and forward the noise signal, as heretofore discussed.

The frequency device may (1) isolate the noise signal for each frequency band over a range of frequency bands; (2) compare the noise signal for each frequency band over the range of frequency bands; and (3) select a drive frequency of the electrical field for the electrical tomography system based on the comparison, as heretofore discussed.

The frequency device may comprise, for examples, individual devices/components as well as combinations thereof. To illustrate, the frequency drive may comprise one or more of a computer console, a personal signal receiver, and a circuitry can.

The computer console, for example, comprises any computer device capable of carrying out the functionality described herein, e.g., an electrical tomography console.

The personal signal receiver, for example, comprises a device capable of receiving a signal such as the personal signal receiver associated with an ingestible event marker (IEM), supra. In one example, the personal signal receiver is configured as a removably attachable device for placement on the human body. In another example, the personal signal receiver is associated with a human being, yet not attached thereto, e.g., in close physical proximity to the human being. In still another example, the personal signal receiver comprises two or more receivers, e.g., three receivers.

The circuitry can comprise any device capable of providing circuit functionality, e.g., a pacemaker can associated with a pacing device. In one example, the circuitry facilitates at least one of electrical stimulation and pacing.

One or more aspect of the subject invention may be in the form of computer readable media having programming stored thereon for implementing the subject methods. The computer readable media may be, for example, in the form of a computer disk or CD, a floppy disc, a magnetic "hard card", a server, or any other computer readable media capable of containing data or the like, stored electronically, magnetically, optically or by other means. Accordingly, stored programming embodying steps for carrying-out the subject methods may be transferred or communicated to a processor, e.g., by using a computer network, server, or other interface connection such as the Internet, or other relay means.

More specifically, the computer readable media may include stored programming embodying an algorithm for carrying out the subject methods. Accordingly, such a stored algorithm is configured to, or is otherwise capable of, practicing the subject methods, e.g., by operating an implantable medical device to perform the subject methods. The subject algorithm and associated processor may also be capable of implementing the appropriate adjustment(s). Of particular interest in certain aspects are systems loaded with such computer readable mediums such that the systems are configured to practice the subject methods.

The previous description of the disclosed aspects is provided to enable any person skilled in the art to make or use the present invention. Various modifications to these aspects will be readily apparent to those skilled in the art, and the generic principles defined herein may be applied to other aspects without departing from the spirit or scope of the invention. Thus, the present disclosure is not intended to be limited to the aspects shown herein but is to be accorded the widest scope consistent with the principles and features disclosed herein.

Although the invention has been described in terms of cardiac motion evaluation aspects, the invention is not so limited, the invention being readily adaptable to evaluation of movement of a wide variety of different tissue locations. The tissue location(s) are generally a defined location or portion of a body, e.g., subject, where in many aspects it is a defined location or portion, i.e., domain or region, of a body structure, such as an organ, where in representative aspects the body structure is an internal body structure, system, or subsystem, such as the spinal column and/or an internal organ, e.g., adrenals, appendix, heart, bladder, brain, eyes, gall bladder, intestines, kidney, liver, lungs, esophagus, ovaries, pancreas, parathyroids, pituitary, prostate, spleen, stomach, testicles, thymus, thyroid, uterus, and veins, etc.

Methods, systems and programming of the invention find use in a variety of different applications. Applications in which the present methods, systems and programming find use include electrical tomography applications, including but not limited to U.S. application Ser. Nos. 11/664,340; 11/731,786; 11/562,690; 12/037,851; 11/219,305; 11/793,904; 12/171,978; 11/909,786; The disclosures of which are herein incorporated by reference. Applications in which the present methods, systems and programming find use include ingestible event markers applications, including but not limited to: PCT application Ser. No. PCT/US2006/016370 published as WO/2006/116718; PCT application Ser. No. PCT/US2007/082563 published as WO/2008/052136; PCT application Ser. No. PCT/US2007/024225 published as WO/2008/063626; PCT application Ser. No. PCT/US2007/022257 published as WO/2008/066617; PCT application Ser. No. PCT/US2008/052845 published as WO/2008/095183; PCT application Ser. No. PCT/US2008/053999 published as WO/2008/101107; PCT application Ser. No. PCT/US2008/056296 published as WO/2008/112577; PCT application Ser. No. PCT/US2008/056299 published as WO/2008/112578; and PCT application Ser. No. PCT/US2008/077753; the disclosures of which are herein incorporated by reference.

What is claimed is:

1. A system for optimally selecting a drive frequency of an electrical tomography, comprising:
    a sensor electrode implanted at a tissue site of a subject to generate an induced signal based on a noise signal over a range of frequency bands, wherein an electrical field for the electrical tomography is turned off;
    a noise processing module to separate the induced signal for each frequency band over the range of frequency bands; and
    a frequency select module to select a drive frequency of the electrical field for the electrical tomography by comparing the induced signal for each frequency band over the range of frequency bands.

2. The system of claim 1, wherein the range of frequency bands is between 50 KHz and 150 KHz.

3. The system of claim 1, wherein a bandwidth of each frequency band comprises 100 Hz.

4. The system of claim 1, wherein the sensor electrode is coupled to the noise processing module via an electrical lead.

5. The system of claim 1, wherein the noise processing module comprises a spectrum analyzer.

6. The system of claim 5, wherein the spectrum analyzer is operable for performing a Fast Fourier Transform of the induced signal.

7. The system of claim 1, wherein the selecting the drive frequency of the electrical field comprises selecting a frequency band with a minimal instantaneous amplitude among the frequency bands.

8. The system of claim 1, wherein the sensor electrode comprises a quadrature amplitude modulator.

9. The system of claim 8, wherein the noise processing module comprises a quadrature amplitude demodulator.

10. The system of claim 9, wherein the quadrature amplitude demodulator comprises a first mixer and a first low pass filter coupled in series to demodulate an in-phase modulated signal (I) and a second mixer and a second low pass filter to demodulate a quadrature-phase modulate signal (Q).

11. The system of claim 10, wherein the noise processing module further comprises a frequency oscillator coupled to the first mixer and the second mixer to sweep across the range of frequency bands.

12. The system of claim 11, wherein the selecting the drive frequency of the electrical field comprises selecting a frequency band with a minimal instantaneous amplitude among the frequency bands.

13. The system of claim 1, wherein the noise processing module comprises a plurality of band pass filters for processing the range of frequency bands.

14. The system of claim 13, wherein the selecting the drive frequency of the electrical field comprises selecting a frequency band with a minimal instantaneous amplitude among respective outputs of the plurality of band pass filters.

15. The system of claim 1, further comprising an electrical field generator module to generate the electrical field with the drive frequency.

16. The system of claim 1, wherein the electrical field is based on a sinusoidal wave.

17. The system of claim 1, wherein the electrical field is based on a spread spectrum signal.

18. A method for optimally selecting a drive frequency of an electrical tomography system, comprising:
    scanning for noise signal processed by a sensor electrode internally located at a tissue site of the electrical tomography system over a range of frequency bands prior to applying an electrical field of the electrical tomography system to the sensor electrode;
    comparing the noise signal processed by the sensor electrode over the range of frequency bands; and
    selecting a frequency band with a minimal noise signal among the range of frequency bands as the drive frequency of the electrical tomography system.

19. The method of claim 18, wherein the noise signal is transmitted via an electrical lead.

20. The method of claim 19, wherein the scanning for the noise signal comprises performing a Fast Fourier Transform of the noise signal accessed at the electrical lead.

21. The method of claim 19, wherein the scanning for the noise signal comprises performing a Discrete Fourier Transform of the noise signal.

22. The method of claim 19, wherein the scanning for the noise signal comprises analyzing energy contents of the range of the frequency bands.

23. The method of claim 18, wherein the range of frequency bands is between 50 KHz and 150 KHz.

24. The method of claim 18, wherein a bandwidth of each frequency band comprises 100 Hz.

25. The method of claim 18, wherein the selecting the drive frequency of the electrical tomography system is performed periodically.

26. The method of claim 18, wherein the electrical field of the drive frequency is based on a sinusoidal wave.

27. The method of claim 18, wherein the electrical field of the drive frequency is based on a spread spectrum signal.

28. A non-transitory computer readable medium for optimally selecting a drive frequency of an electrical tomography system having instructions that, when executed by a computer, cause the computer to perform a method comprising:
    scanning for noise signal processed by a sensor electrode, which is implanted at a tissue site, of an electrical tomography system over a range of frequency bands prior to applying an electrical field of the electrical tomography system to the sensor electrode;
    comparing the noise signal processed by the sensor electrode over the range of frequency bands; and selecting a frequency band with a minimal noise signal among the range of frequency bands as the drive frequency of the electrical tomography system.

29. A system for selecting a drive frequency of an electrical tomography, comprising:
- a sensor electrode implanted at an internal tissue site of a subject to generate a signal through induction, wherein the signal represents the power level of a noise signal over a range of frequency bands when an electrical field used to produce the electrical tomography is turned off;
- a noise processing module to separate the signal for each frequency band over the range of frequency bands; and
- a frequency select module to select a drive frequency of the electrical field for the electrical tomography by comparing the signal for each frequency band over the range of frequency bands.

* * * * *

UNITED STATES PATENT AND TRADEMARK OFFICE
CERTIFICATE OF CORRECTION

PATENT NO. : 7,969,161 B2  
APPLICATION NO. : 12/665514  
DATED : June 28, 2011  
INVENTOR(S) : Yashar Behzadi Page 1 of 1

It is certified that error appears in the above-identified patent and that said Letters Patent is hereby corrected as shown below:

Title page, Item (73) Assignee: "Proteus Bomedical, Inc." should be replaced with -- Proteus Biomedical, Inc. --

Signed and Sealed this  
Thirty-first Day of January, 2012

David J. Kappos  
*Director of the United States Patent and Trademark Office*